United States Patent
Normand et al.

(10) Patent No.: US 10,640,479 B2
(45) Date of Patent: May 5, 2020

(54) PROFLAVOR DELIVERY POWDERS

(71) Applicant: Firmenich SA, Satigny (CH)

(72) Inventors: Valery Normand, Plainsboro, NJ (US); Rutger M. T. Van Sleeuwen, Plainsboro, NJ (US)

(73) Assignee: Firmenich SA, Satigny (CH)

( * ) Notice: Subject to any disclaimer, the term of this patent is extended or adjusted under 35 U.S.C. 154(b) by 148 days.

(21) Appl. No.: 15/539,391

(22) PCT Filed: Dec. 21, 2015

(86) PCT No.: PCT/EP2015/080722
§ 371 (c)(1),
(2) Date: Jun. 23, 2017

(87) PCT Pub. No.: WO2016/102428
PCT Pub. Date: Jun. 30, 2016

(65) Prior Publication Data
US 2017/0369461 A1 Dec. 28, 2017

Related U.S. Application Data

(60) Provisional application No. 62/096,842, filed on Dec. 24, 2014.

(51) Int. Cl.
| | | |
|---|---|---|
| *A23L 27/29* | (2016.01) | |
| *A23L 2/56* | (2006.01) | |
| *C07D 307/12* | (2006.01) | |
| *C07C 69/44* | (2006.01) | |
| *A23L 27/20* | (2016.01) | |
| *C07C 69/60* | (2006.01) | |
| *C07C 69/38* | (2006.01) | |
| *C07C 69/40* | (2006.01) | |
| *C07C 45/42* | (2006.01) | |
| *C07C 69/003* | (2006.01) | |

(52) U.S. Cl.
CPC .............. *C07D 307/12* (2013.01); *A23L 2/56* (2013.01); *A23L 27/2024* (2016.08); *A23L 27/29* (2016.08); *C07C 45/42* (2013.01); *C07C 69/003* (2013.01); *C07C 69/38* (2013.01); *C07C 69/40* (2013.01); *C07C 69/44* (2013.01); *C07C 69/60* (2013.01); *A23V 2002/00* (2013.01)

(58) Field of Classification Search
CPC ........ A23L 27/2024; A23L 27/29; A23L 2/56; A23L 27/72; C07C 69/38; C07C 69/40; C07C 69/44; C07C 69/60; C07D 307/12
See application file for complete search history.

(56) References Cited

U.S. PATENT DOCUMENTS

| | | | | |
|---|---|---|---|---|
| 4,419,280 | A * | 12/1983 | Boden | C11B 9/0019 |
| | | | | 512/26 |
| 5,079,023 | A | 1/1992 | DeSimone | |
| 6,235,956 | B1 * | 5/2001 | Hugues | C07C 43/303 |
| | | | | 585/511 |
| 2005/0026998 | A1 | 2/2005 | Womack et al. | |
| 2012/0184474 | A1 | 7/2012 | Kawata et al. | |
| 2012/0270979 | A1 | 10/2012 | Hsu et al. | |
| 2015/0232691 | A1 * | 8/2015 | Webster | C08F 222/02 |
| | | | | 523/400 |
| 2017/0044089 | A1 * | 2/2017 | Messana | C08F 2/44 |
| 2017/0339993 | A1 * | 11/2017 | Womack | A23L 27/2024 |
| 2018/0103667 | A1 * | 4/2018 | Womack | A23L 27/2024 |

FOREIGN PATENT DOCUMENTS

| | | |
|---|---|---|
| JP | 2004094161 A | 3/2004 |
| JP | 2013182040 A | 9/2013 |
| WO | WO2014043720 A1 | 3/2014 |
| WO | WO-2014206956 A1 * 12/2014 | ............. A23P 10/35 |

OTHER PUBLICATIONS

Lukic et al "Characterization and Differentiation of Monovarietal Grape Marc Distillates on the Basis of Varietal Aroma Compound Composition", Journal of Agricultural and Food Chemistry, 2010, 58(12), pp. 7351-7360.*
Sorrel, Chapter 19.1d, Organic Chemistry, 2nd Edition, University Science Books, 2006.*
International Search Report and Written Opinion, application PCT/EP2015/080722 dated Mar. 31, 2016.
Williams et al, "Hydroxylated Linalool Derivatives as Precursors of Volatile Monoterpenes of Muscat Grapes," J. Agric. Food Chem., vol. 28, No. 4, 1980, pp. 766-771.
Furia et al, "Fenaroli's Handbook of Flavor Ingredients," XP-002102351, 1975, pp. 543, 656.
Yamamoto et al, "New thermosetting coatings using blocked carboxyl groups," Progress in Organic Coatings, vol. 40, No. 1-4, 2000, pp. 267-273.
Kovash et al, "Thermoset Coatings from Epoxidized Sucrose Soyate and Blocked, Bio-Based DiCarboxylic Acids," ChemSusChem, 2014, vol. 7, No. 8, pp. 2289-2294.

* cited by examiner

*Primary Examiner* — Nikki H. Dees
*Assistant Examiner* — Changqing Li
(74) *Attorney, Agent, or Firm* — Armstrong Teasdale LLP

(57) ABSTRACT

Provided herein are formulations of plated powders of acetaldehyde precursors. Also provided herein are methods of making and using the powders.

12 Claims, No Drawings

PROFLAVOR DELIVERY POWDERS

RELATED APPLICATIONS

This application is a national stage application under 35 U.S.C. § 371 filing of International Patent Application PCT/EP2015/080722, filed Dec. 21, 2015, which claims the benefit of U.S. Provisional Application 62/096,842, filed Dec. 24, 2014.

FIELD

Provided herein are precursors (proflavors) to acetaldehyde and their use for delivering acetaldehyde to food and beverages to typically provide increase flavor.

BACKGROUND

Acetaldehyde is an important, yet difficult to encapsulate flavor ingredient. It is used in a large variety of flavors but is particularly appreciated in fruit flavors where it imparts important aspects of freshness and juiciness to the flavors. The volatility of acetaldehyde also provides lift to the aroma greatly contributing to the olfactive impact of the flavor. Thus the use of acetaldehyde is indispensable for creating flavors where these effects are desired such as in beverages. However, with a boiling point of 20-21° C., it is a difficult material to use due to evaporation during handling which in turn can create unsafe situations due to overexposure to personnel and the risk of fire. Once incorporated into a liquid flavor, loss of acetaldehyde due to evaporation is still a concern which also can make handling such flavors difficult. In addition to being highly volatile, acetaldehyde is a very reactive chemical. It can react with alcohols in flavor formulations to form acetals; it can engage in aldol condensation reactions; it is susceptible to oxidation; and it can trimerize to form paraldehyde. In addition to losing acetaldehyde by these chemical reactions, the products formed can change the character of the flavor and in the worst case contribute unwanted off-flavors.

A simple and cost effective formulation of acetaldehyde precursors is desired for example, to simply mix an acetaldehyde precursor with a carrier.

SUMMARY

Provided herein is a plated powder comprising:
a) a compound selected from the group consisting of a compound of Formula I

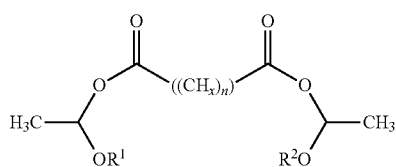

wherein R1 and R2 are independently selected from a branched or straight $C_1$-$C_6$ and a $C_1$-$C_6$ alkenyl, n is 1, 2, 3, 4, 5 or 6 and x is independently 0, 1 or 2 provided that when n is 1, x is 2, and 5-(2-(1-ethoxyethoxy)propan-2-yl)-2-methyl-2-vinyltetrahydrofuran; and b) a carrier.

Further provided herein is a method of releasing acetaldehyde into an aqueous solution comprising delivering a plated powder as described above to the aqueous solution.

In a further embodiment provided herein is the use of a plated powder as described above to confer, enhance, improve or modify the flavor or aroma of a flavored article.

DESCRIPTION OF THE INVENTION

For the Summary, Description and Claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of".

5-(2-(1-ethoxyethoxy)propan-2-yl)-2-methyl-2-vinyltetrahydrofuran is represented by the formula

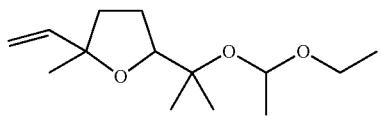 [SMILES: C=CC1(C)CCC(C(C)(C)OC(C)OCC)O1]

Plating is defined as coating a thin layer of substance onto a solid surface; the carrier. In one embodiment, the carrier is a free flowing powder, particularly one having a microporous matrix.

In one embodiment, the carrier is selected from the group consisting of sugars, salts, maltodextrins, dextrins silicon dioxide, starches, gums and hydrocolloids. In one embodiment the sugars are selected from the group consisting of dextrose, fructose, sucrose, and lactose. In a particular embodiment, the salt comprises sodium chloride. In one embodiment the Carrier is Maltodextrin, particularly 18 DE. In another embodiment the carrier is a tapioca maltodextrin, for example but not limited to N-Zorbi® (Ingredion).

Loading levels of the liquid compounds onto the carrier powders provided here are from about 1% to about 70% by weight, particularly from about 5% to 40%, more particularly from about 10% to about 30%, and even more particularly from about 15% to about 25%.

In some embodiments the carrier powder comprises the compound provided herein in an amount of greater than or equal to 0.01% up to about 15%, by weight, of the total weight of the powder. In another particular embodiment, the compounds provided herein are provided in an amount of about 1% to 15%, particularly from 1% to 5%, and more particularly from about 1% to 2%, of the total weight of the powder.

In one embodiment, the carrier and the compounds provided here are mixed in any suitable mixer vessel, for example, but not limited to a paddle mixer, ribbon blender, or a V-blender. A mortar and pestle may also be used.

The compounds provided herein are precursors of acetaldehyde in that they act as a "proflavor" and release acetaldehyde by hydrolysis when exposed to water.

The compounds provided herein comprise a compound of Formula I wherein $R^1$ and R are independently a straight or branched $C_1$-$C_6$ alkyl.

In one embodiment, provided herein is a compound of Formula I wherein $R^1$ and $R^2$ are independently selected from the group consisting of methyl, ethyl, propyl, and butyl.

In another embodiment, provided herein is a compound of Formula I wherein n is 1 and x is 2.

In another embodiment, provided herein is a compound of Formula I wherein n is 2 and x is independently 0, 1 or 2.

In another embodiment, provided herein is a compound of Formula I wherein n is 3, 4, 5 or 6 and x is independently 0, 1 or 2.

In another embodiment provided herein is a compound of Formula I selected from the group consisting of: bis(1-ethoxyethyl) succinate; bis(1-ethoxyethyl) adipate; bis(1-ethoxyethyl) fumarate; bis(1-propoxyethyl) succinate; bis(1-propoxyethyl) adipate; bis(1-propoxyethyl) fumarate; bis(1-butoxyethyl) succinate; bis(1-butoxyethyl) adipate, and bis(1-butoxyethyl) fumarate.

In a particular provided herein is a compound of Formula I selected from the group consisting of bis(1-ethoxyethyl) succinate; bis(1-ethoxyethyl) adipate; bis(1-ethoxyethyl) fumarate; bis(1-propoxyethyl) succinate; bis(1-propoxyethyl) adipate; bis(1-propoxyethyl) fumarate; bis(1-butoxyethyl) succinate; and bis(1-butoxyethyl) adipate In another embodiment, provided herein is a compound of Formula I comprising bis(1-ethoxyethyl) succinate.

In another embodiment provided herein is a compound of Formula I comprising bis(1-propoxyethyl) succinate.

In another embodiment provided herein is a compound of Formula I comprising bis(1-butoxyethyl) succinate.

In another embodiment provided herein is a compound of Formula I comprising bis(1-ethoxyethyl) adipate, In another embodiment provided herein is a compound of Formula I comprising bis(1-propoxyethyl) adipate.

In another embodiment provided herein is a compound of Formula I comprising bis(1-butoxyethyl) adipate.

In another embodiment provided herein is a compound of Formula I comprising bis(1-ethoxyethyl) fumarate.

In another embodiment provided herein is a compound of Formula I comprising bis(1-propoxyethyl) fumarate.

In another embodiment provided herein is a compound of Formula I comprising bis(1-butoxyethyl) fumarate.

In another embodiment provided herein is a compound 5-(2-(1-ethoxyethoxy)propan-2-yl)-2-methyl-2-vinyltetrahydrofuran.

The compounds provided herein and the methods of making them can be found in U.S. Provisional Application Nos. 62/096,830 and 62/096,835 file on even date herewith. The contents of both applications are incorporated by reference in their entirety herein. The plated powders provided herein may also additionally comprise a flavor. In a particular embodiment the flavors have a Log P of >2 with a Mw<600 Daltons. The compositions provided herein may also additionally comprise a flavor. In a particular embodiment the flavors have a Log P of >2 with a Mw<600 Daltons.

The powders provided herein may further comprise a flavor. This flavor may provide additional stability to the plated proflavor, since this flavor may act as a solvent for the proflavor. This can help to lower the exposure of the proflavor to moisture (from atmosphere or from the carrier) and therefore reduce the hydrolysis rate during storage. Additionally, the flavor may already be encapsulated within the plating powder, such as a spray dried flavor. By use of the word "Flavor" it is meant here a flavoring ingredient or a mixture of flavoring ingredients, solvents or adjuvants of current use for the preparation of a flavoring formulation, i.e. a particular mixture of ingredients which is intended to be added to an edible composition or chewable product to impart, improve or modify its organoleptic properties, in particular its flavor and/or taste. Flavoring ingredients are well known to a person skilled in the art and their nature does not warrant a detailed description here, which in any case would not be exhaustive, the skilled flavorist being able to select them on the basis of his general knowledge and according to the intended use or application and the organoleptic effect it is desired to achieve. Many of these flavoring ingredients are listed in reference texts such as in the book by S. Arctander, Perfume and Flavor Chemicals, 1969, Montclair, N.J., USA, or its more recent versions, or in other works of similar nature such as Fenaroli's Handbook of Flavor Ingredients, 1975, CRC Press or Synthetic Food Adjuncts, 1947, by M. B. Jacobs, van Nostrand Co., Inc. Solvents and adjuvants of current use for the preparation of a flavoring formulation are also well known in the art.

The phrase flavor includes not only flavors that impart or modify the smell of foods but include taste imparting or modifying ingredients. The latter do not necessarily have a taste or smell themselves but are capable of modifying the taste that other ingredients provide, for instance, salt enhancing ingredients, sweetness enhancing ingredients, umami enhancing ingredients, bitterness blocking ingredients and so on.

In a further embodiment, suitable sweetening components may be included in the powders described herein. In a particular embodiment, a sweetening component is selected from the group consisting of sugar (e.g., but not limited to sucrose), a stevia component (such as but not limited to stevioside or rebaudioside A), sodium cyclamate, aspartame, sucralose, sodium saccharine, and Acesulfame K or mixtures thereof.

In one embodiment, the compositions and compounds provided herein provide "fresh", "juicy" and "fruity" flavor and/or aroma to a food article.

A plated powder provided herein containing a compound selected from the group consisting of a compound of formula (I) and 5-(2-(1-ethoxyethoxy)propan-2-yl)-2-methyl-2-vinyltetrahydrofuran can be incorporated into a flavored articles to positively impart, or modify, the freshness or fruity flavor or aroma of said articles. Thus, in yet another aspect, the present invention provides a flavored article comprising:
 i) a plated powder comprising a compound selected from the group consisting of formula (I) and 5-(2-(1-ethoxyethoxy)propan-2-yl)-2-methyl-2-vinyltetrahydrofuran, as above, and
 ii) a foodstuff base.

The compositions provided herein may also additionally comprise a flavor. In a particular embodiment the flavors have a Log P of >2 with a Mw<600 Daltons.

The powders provided herein may further comprise an additional flavor.

A powder provided herein containing a compound selected from the group consisting of a compound of formula (I) and 5-(2-(1-ethoxyethoxy)propan-2-yl)-2-methyl-2-vinyltetrahydrofuran can be incorporated into a flavored articles to positively impart, or modify, the freshness or fruity flavor or aroma of said articles. Thus, in yet another aspect, the present invention provides a flavored article comprising:
 i) a powder comprising a compound selected from the group consisting of formula (I) and 5-(2-(1-ethoxyethoxy)propan-2-yl)-2-methyl-2-vinyltetrahydrofuran, as defined and
 ii) a foodstuff base.

For the sake of clarity, it has to be mentioned that, by "foodstuff" we mean here an edible product, e.g. a food or a beverage. Therefore, a flavored article according to the invention comprises one or more compounds according to formula (I) or 5-(2-(1-ethoxyethoxy)propan-2-yl)-2-methyl-2-vinyltetrahydrofuran, as well as optional benefit agents, corresponding to a flavor or aroma profile of the desired edible product. The compositions and methods provided herein have use in food or beverage products. When the food product is a particulate or powdery food, the dry powders may easily be added thereto by dry-mixing. Typical food products are selected from the group consisting of an instant soup or sauce, a breakfast cereal, a powdered milk, a baby food, a powdered drink, a powdered chocolate drink, a spread, a powdered cereal drink, a chewing gum, an effervescent tablet, a cereal bar, and a chocolate bar. The powdered foods or drinks may be intended to be consumed after reconstitution of the product with water, milk and/or a juice, or another aqueous liquid.

Suitable foodstuff bases, e.g. foods or beverages, include dairy and confectionary products where a fresh or fruity tonality is desired.

In another embodiment provided herein is a fluid dairy product including without limitation, non-frozen, partially frozen and frozen fluid dairy products such as, for example, milks, ice creams, sorbets and yogurts.

Beverage products include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tealeaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra high temperature, ohmic heating or commercial aseptic sterilization) and hot-filled packaging; and cold-filled products made through filtration or other preservation techniques. The nature and type of the constituents of the foodstuffs or beverages do not warrant a more detailed description here, the skilled person being able to select them on the basis of his general knowledge and according to the nature of said product.

In one embodiment, a compound provided herein is provided in the powder or bead in an amount that ranges by weight, of about 0.01% to 15%, particularly from about 1% to about 15%, more particularly from about 1% to about 5%, and more particularly from about 1% to about 2% of the total weight of the powder. In one embodiment, the concentration of the compounds provided herein (delivered as a powder) in a flavored article are in the range, by weight, of about 3 ppm to about 60 ppm, particularly from about 3 ppm to about 30 ppm, more particularly from about 12 ppm to about 30 ppm, even more particularly from about 12 ppm to 15 ppm based on the total weight of the flavored article.

In another embodiment, the compounds provided herein are provided in an amount in a flavored article such that the powders release a compound provided herein that further release acetaldehyde in the flavored article when exposed to an aqueous solution wherein the acetaldehyde is released in an amount that ranges from about 1 ppm to about 20 ppm, more particularly from about 1 ppm to about 10 ppm, more particularly from 4 ppm to about 10 ppm, even more particularly from about 4 ppm to about 5 ppm of the total weight of the article.

The following Examples are illustrative only and are not meant to limit the scope of the claims, the Summary or any invention presented herein.

EXAMPLES

Plating of Acetaldehyde Precursors on Carbohydrate or Other Matrices

Two proflavors plated on two matrices were prepared. The approximate formulations in weight % are summarized in Table 1 and a more detailed explanation is given below for each of the examples.

TABLE 1

Summary of composition of various plated samples

| Compound | Example 1 Formulation in Weight % | Example 2 Formulation in Weight % | Example 3 Formulation in Weight % | Example 4 Formulation in Weight % |
| --- | --- | --- | --- | --- |
| 5-(2-(1-ethoxyethoxy)propan-2-yl)-2-methyl-2-vinyltetrahydrofuran | 10 | 10 | — | — |
| bis(1-ethoxyethyl) adipate | — | — | 10 | 10 |
| Maltodextrin (Glucidex IT 19, Roquette Corporation, Lestrem, France | 90 | — | 90 | — |
| N-Zorbit ® (Ingredion) | — | 90 | — | 90 |

Example 1

A Mortar Grinder RM200 (Retsch Inc, Newtown Pa.) was used to plate the flavor precursor onto a carrier. Maltodextrin 18DE (plating carrier) was dosed into the mortar grinder while it was running. Then approximately 10 wt % 5-(2-(1-ethoxyethoxy)propan-2-yl)-2-methyl-2-vinyltetrahydrofuran was dosed gradually on top of the powder while mixing. The powder was mixed for an additional two minutes.

The composition of the powder mixture obtained was analyzed by GC with MS detection. Proflavor (and possible reaction products generated during process) were extracted from the plated powder for analysis by adding 5 ml of ethyl acetate to 100 mg of flavor powder. The 5-(2-(1-ethoxyethoxy)propan-2-yl)-2-methyl-2-vinyltetrahydrofuran content was found to be 94.1% of the extracted extracted compounds. Linalool oxide was found at 3.0%, so indicating that very little reaction of the proflavor had occurred during the process.

Example 2

A Mortar Grinder RM200 (Retsch Inc, Newtown Pa.) was used to plate the flavor precursor onto a matrix. N-Zorbit® (plating carrier) was dosed into the mortar grinder while it was running. Then approximately 10 wt % 5-(2-(1-ethoxyethoxy)propan-2-yl)-2-methyl-2-vinyltetrahydrofuran was dosed gradually on top of the powder while mixing. The powder was mixed for an additional two minutes.

The powder was analyzed by GC with MS detection. Proflavor (and possible reaction products generated during process) was extracted from the plated powder for analysis by adding 5 ml of ethyl acetate to 100 mg of flavor powder. The 5-(2-(1-ethoxyethoxy)propan-2-yl)-2-methyl-2-vinyltetrahydrofuran content was found to be 95.8% of the extracted components. Linalool oxide was found at 1.9%, so very little reaction of the proflavor had occurred during the process.

Example 3

A Mortar Grinder RM200 (Retsch Inc, Newtown Pa.) was used to plate the flavor precursor onto a carrier. Maltodextrin 18DE (plating carrier) was dosed into the mortar grinder while it was running. Then approximately 10 wt % bis(1-ethoxyethyl) adipate was dosed gradually on top of the powder while mixing. The powder was mixed for an additional two minutes.

The powder was analyzed by GC with MS detection. Proflavor (and possible reaction products generated during process) was extracted from the plated powder for analysis by adding 5 ml of ethyl acetate to 100 mg of flavor powder.

The bis(1-ethoxyethyl) adipate content was found to be 100% of the extracted compounds. This implies that no reaction of the proflavor has occurred during the process.

Example 4

A Mortar Grinder RM200 (Retsch Inc, Newtown Pa.) was used to plate the flavor precursor onto a carrier. N-Zorbit (plating carrier) was dosed into the mortar grinder while it was running. Then approximately 10 wt % bis(1-ethoxyethyl) adipate was dosed gradually on top of the powder while mixing. The powder was mixed for an additional two minutes.

The powder was analyzed by GC with MS detection. Proflavor (and possible reaction products generated during process) was extracted from the plated powder for analysis by adding 5 ml of ethyl acetate to 100 mg of flavor powder.

The bis(1-ethoxyethyl) adipate content was found to be 100% of the components extracted. This implies that no reaction of the proflavor has occurred during the process.

Example 5a

A Mortar Grinder RM200 (Retsch Inc, Newtown Pa.) was used to plate the flavor precursor onto a carrier. Maltodextrin 18DE (plating carrier) was dosed into the mortar grinder while it was running. Then approximately 1.5 wt % 5-(2-(1-ethoxyethoxy)propan-2-yl)-2-methyl-2-vinyltetrahydrofuran was dosed gradually on top of the powder while mixing. The powder was mixed for an additional two minutes.

Example 5b

A Mortar Grinder RM200 (Retsch Inc, Newtown Pa.) was used to plate the flavor precursor onto a carrier. Maltodextrin 18DE (plating carrier) was dosed into the mortar grinder while it was running. Then approximately 1.5 wt % 5-(2-(1-ethoxyethoxy)propan-2-yl)-2-methyl-2-vinyltetrahydrofuran and 4.5 wt % of orange oil was plated onto this powder. The powder was mixed for an additional two minutes.

The compositions of the powder mixtures 5a and 5b were analyzed for total amount of acetaldehyde that can be released. The proflavor in the particles was converted to acetaldehyde by an acid-catalyzed hydrolysis and the total acetaldehyde content was analyzed by HPLC with UV/VIS detection after DNPH (2,4-dinitrophenylhydrazine) derivatization. The acetaldehyde released from sample 5a was found to be 0.22% on total wet basis. 5-(2-(1-ethoxyethoxy)propan-2-yl)-2-methyl-2-vinyltetrahydrofuran has a maximum theoretical yield of 18.1% by mass; this means that 1 gram of proflavor can release 0.181 g acetaldehyde if completely converted. Therefore, the acetaldehyde retention (proflavor+acetaldehyde) was high ~82%. The acetaldehyde released from sample 5b was found to be 0.35% on total wet basis. Therefore, the acetaldehyde retention (proflavor+acetaldehyde) was high~>100%. The addition of orange oil during the plating process helped to better preserve the proflavor, resulting in higher levels of acetaldehyde that can be released from this powder.

Example 6a

A Mortar Grinder RM200 (Retsch Inc, Newtown Pa.) was used to plate the flavor precursor onto a carrier. N-Zorbit (plating carrier) was dosed into the mortar grinder while it was running. Then approximately 1.5 wt % 5-(2-(1-ethoxyethoxy)propan-2-yl)-2-methyl-2-vinyltetrahydrofuran was dosed gradually on top of the powder while mixing. The powder was mixed for an additional two minutes.

Example 6b

A Mortar Grinder RM200 (Retsch Inc, Newtown Pa.) was used to plate the flavor precursor onto a carrier. N-Zorbit (plating carrier) was dosed into the mortar grinder while it was running. Then approximately 1.5 wt % 5-(2-(1-ethoxyethoxy)propan-2-yl)-2-methyl-2-vinyltetrahydrofuran and 4.5 wt % of orange oil was plated onto this powder. The powder was mixed for an additional two minutes.

The compositions of the powder mixtures 6a and 6b were analyzed for total amount of acetaldehyde that can be released. The proflavor in the particles was converted to acetaldehyde by an acid-catalyzed hydrolysis and the total acetaldehyde content was analyzed by HPLC with UV/VIS detection after DNPH (2,4-dinitrophenylhydrazine) derivatization. The acetaldehyde released from sample 6a was found to be 0.16% on total wet basis. 5-(2-(1-ethoxyethoxy)propan-2-yl)-2-methyl-2-vinyltetrahydrofuran has a maximum theoretical yield of 18.1% by mass; this means that 1 gram of proflavor can release 0.181 g acetaldehyde if completely converted. Therefore, the acetaldehyde retention (proflavor+acetaldehyde) was satisfactory ~59%. The acetaldehyde released from sample 6b was found to be 0.31% on total wet basis. Therefore, the acetaldehyde retention (proflavor+acetaldehyde) was high ~>100%. The addition of orange oil during the plating process helped to better preserve the proflavor, resulting in higher levels of acetaldehyde that can be released from this powder.

Example 7a

A Mortar Grinder RM200 (Retsch Inc, Newtown Pa.) was used to plate the flavor precursor onto a carrier. Maltodextrin 18DE (plating carrier) was dosed into the mortar grinder while it was running. Then approximately 1.5 wt % bis(1-ethoxyethyl) adipate was dosed gradually on top of the powder while mixing. The powder was mixed for an additional two minutes.

Example 7b

A Mortar Grinder RM200 (Retsch Inc, Newtown Pa.) was used to plate the flavor precursor onto a carrier. Maltodextrin 18DE (plating carrier) was dosed into the mortar grinder while it was running. Then approximately 1.5 wt % bis(1-ethoxyethyl) adipate and 4.5 wt % of orange oil was plated onto this powder. The powder was mixed for an additional two minutes.

The compositions of the powder mixtures 7a and 7b were analyzed for total amount of acetaldehyde that can be released. The proflavor in the particles was converted to acetaldehyde by an acid-catalyzed hydrolysis and the total acetaldehyde content was analyzed by HPLC with UV/VIS detection after DNPH (2,4-dinitrophenylhydrazine) derivatization. The acetaldehyde released from sample 7a was found to be 0.33% on total wet basis. Bis(1-ethoxyethyl) adipate has a maximum theoretical yield of 30.3% by mass; this means that 1 gram of proflavor can release 0.303 g acetaldehyde if completely converted. Therefore, the acetaldehyde retention (proflavor+acetaldehyde) was acceptable ~72%. The acetaldehyde released from sample 7b was found to be 0.53% on total wet basis. Therefore, the acetaldehyde retention (proflavor+acetaldehyde) was high ~>100%. The addition of orange oil during the plating process helped to better preserve the proflavor, resulting in higher levels of acetaldehyde that can be released from this powder.

Example 8a

A Mortar Grinder RM200 (Retsch Inc, Newtown Pa.) was used to plate the flavor precursor onto a carrier. N-Zorbit (plating carrier) was dosed into the mortar grinder while it was running. Then approximately 1.5 wt % bis(1-ethoxyethyl) adipate was dosed gradually on top of the powder while mixing. The powder was mixed for an additional two minutes.

Example 8b

A Mortar Grinder RM200 (Retsch Inc, Newtown Pa.) was used to plate the flavor precursor onto a carrier. N-Zorbit (plating carrier) was dosed into the mortar grinder while it was running. Then approximately 1.5 wt % bis(l-ethoxyethyl) adipate and 4.5 wt % of orange oil was plated onto this powder. The powder was mixed for an additional two minutes.

The compositions of the powder mixtures 8a and 8b were analyzed for total amount of acetaldehyde that can be released. The proflavor in the particles was converted to acetaldehyde by an acid-catalyzed hydrolysis and the total acetaldehyde content was analyzed by HPLC with UV/VIS detection after DNPH (2,4-dinitrophenylhydrazine) derivatization. The acetaldehyde released from sample 8a was found to be 0.24% on total wet basis. Bis(1-ethoxyethyl) adipate has a maximum theoretical yield of 30.3% by mass; this means that 1 gram of proflavor can release 0.303 g acetaldehyde if completely converted. Therefore, the actual approximate acetaldehyde retention (proflavor+acetaldehyde) was satisfactory ~53%. The acetaldehyde released from sample 8b was found to be 0.50% on total wet basis. Therefore, the acetaldehyde retention (proflavor+acetaldehyde) was high ~>100%. The addition of orange oil during the plating process helped to better preserve the proflavor, resulting in higher levels of acetaldehyde that can be released from this powder.

Example 9

Tasting of Beverages Containing Different Acetaldehyde Precursors and Orange Flavor Plated onto Various Carriers Two proflavors were evaluated on three different carriers. Plated powders were made using 100 ml beaker and a plastic spoon for mixing. Liquid and powder ingredients were mixed together for a least 10 minutes. The approximate formulations of the powders in weight % are summarized in Table 2. These samples were diluted in a tasting solution (7% sugar+0.07% citric acid in spring water) to obtain expected acetaldehyde concentrations as noted in Table 2. Control beverages (contains everything except the proflavor, Samples 1, 4 and 8) also were prepared for comparison. A small team of panelists tasted the samples in Table 2 in two separate sets @~4 ppm acetaldehyde and ~0.0066% orange oil in a model tasting solution of 7% sugar+0.07% citric acid.

Set 1: Samples 1-6

The samples of proflavor plated on maltodextrin and N-Zorbit (2, 3, and 5, 6) all tasted better than the control samples (1 and 4) with higher flavor intensity and were juicier, fresher, and more orangey.

Set 2: Samples 7-8

The spray dried proflavor sample (7) was clearly nicer than the control (8) with higher flavor intensity.

TABLE 2

Summary of composition of various plated samples and results of tasting

| Ingredients | Sample 1 | Sample 2 | Sample 3 | Sample 4 | Sample 5 | Sample 6 | Sample 7 | Sample 8 |
|---|---|---|---|---|---|---|---|---|
| 5-(2-(1-ethoxyethoxy)propan-2-yl)-2-methyl-2-vinyltetrahydrofuran | | 1.5% | | | 1.5% | | 8.1% | |
| bis(1-ethoxyethyl) adipate | | | 1.5% | | | 1.5% | | |
| Orange Oil California ARR 968585 (Sunkist Growers) | 4.5% | 4.5% | 4.5% | 4.5% | 4.5% | 4.5% | | |
| Maltodextrin (Glucidex IT19, Roquette Corporation, Lestrem, France) | 95.5% | 94% | 94% | | | | | |
| N-Zorbit | | | | 95.5% | 94% | 94% | | |
| Orange Spray Dried Powder (~26% orange oil loading) | | | | | | | 91.9% | 100% |
| Theoretical Acetaldehyde Content in beverage if 100% conversion and no losses | 0 ppm | 3.8 ppm | 3.8 ppm | 0 ppm | 4.7 ppm | 4.7 ppm | 4.3 ppm | 0 ppm |

TABLE 2-continued

Summary of composition of various plated samples and results of tasting

| Ingredients | Sample 1 | Sample 2 | Sample 3 | Sample 4 | Sample 5 | Sample 6 | Sample 7 | Sample 8 |
|---|---|---|---|---|---|---|---|---|
| Average Flavor Intensity | 4.0 | 7.0 | 6.5 | 4 | 7 | 6.5 | NA | NA |
| Comments | orangey but flat, low impact | sweet, juicy, fresh, more orangey, fruity juicy odor | sweet, juicy, fresh, orangey, | flat, low impact | sweet, juicy, ripe, fresh, nice juicy odor | sweet, juicy, fresh, nice juicy odor | flavor more intense, juicier than sample 8 control | |

The invention claimed is:

1. A plated powder comprising:
   a) a compound selected from the group consisting of a compound of Formula I

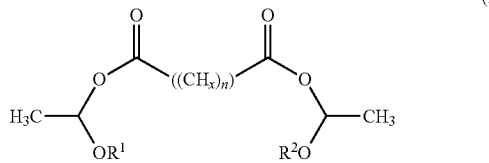

(I)

wherein $R^1$ and $R^2$ are independently selected from a branched or straight $C_1$-$C_6$ alkyl and a $C_1$-$C_4$ alkenyl, n is 1, 2, 3, 4, 5 or 6 and x is independently 0, 1 or 2 provided that when n is 1, x is 2, and 5-(2-(1-ethoxyethoxy)propan-2-yl)-2-methyl-2-vinyltetrahydrofuran; and
   b) a carrier.

2. The compound as recited in claim 1 wherein $R^1$ and $R^2$ are independently a straight or branched $C_1$-$C_4$ alkyl.

3. The compound as recited in claim 2 wherein $R^1$ and $R^2$ are independently selected from the group consisting of methyl, ethyl, propyl, and butyl.

4. The compound as recited in claim 1 wherein n is 1 and x is 2.

5. The compound as recited in claim 1 wherein n is 2 and x is independently 0, 1 or 2.

6. The compound as recited in claim 1 wherein n is 3, 4, 5 or 6 and x is independently 0, 1 or 2.

7. The plated powder as recited in claim 1, wherein the compound of Formula I is selected from the group consisting of bis(1-ethoxyethyl) succinate; bis(1-ethoxyethyl) adipate; bis(1-ethoxyethyl) fumarate; bis(1-propoxyethyl) succinate: bis (1-propoxyethyl) adipate: bis(1-propoxyethyl) fumarate; bis(1-butoxyethyl) succinate; bis(1-butoxyethyl) adipate, and bis(1-butoxyethyl) fumarate.

8. The plated powder as recited in claim 1, wherein the compound of Formula I is 5-(2-(1-ethoxyethoxy)propan-2-yl)-2-methyl-2-vinyltetrahydrofuran.

9. A method of releasing acetaldehyde into an aqueous solution comprising delivering the plated powder as recited in claim 1 to an aqueous solution.

10. A method of conferring, enhancing, improving or modifying the flavor or aroma of a flavored article comprising combining the plated powder as recited in claim 1 in a flavored article, wherein the flavored article has an enhanced, improved or modified flavor or aroma compared to a flavored article that does not contain the compound.

11. A method of making a plated powder comprising:
   i) mixing a compound as defined in claim 1 and a carrier.

12. A flavored article, wherein the flavored article comprises the plated powder as recited in claim 1.

* * * * *

UNITED STATES PATENT AND TRADEMARK OFFICE
CERTIFICATE OF CORRECTION

| | |
|---|---|
| PATENT NO. | : 10,640,479 B2 |
| APPLICATION NO. | : 15/539391 |
| DATED | : May 5, 2020 |
| INVENTOR(S) | : Valery Normand |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 233 days.

Signed and Sealed this
Tenth Day of January, 2023

Katherine Kelly Vidal
*Director of the United States Patent and Trademark Office*